United States Patent [19]

Bramberga et al.

[11] 3,957,034
[45] May 18, 1976

[54] METHOD OF CYTOLOGICAL DIAGNOSTICATION OF PRECANCER AND CANCER

[76] Inventors: Velta Mikelevna Bramberga, ulitsa Gregora, 8. kv. 20; Teodor Arvidovich Grendze, ulitsa Suvorova, 16, kv. 24; Daina Arvidovna Plegere, ulitsa Dzelzevas 15/2, Korpus 2, kv. 34; Arkady Yakovlevich Khesin, ulitsa Suvorova, 16, kv. 18; Etil Kharaldovich Smiltniex, ulitsa Aglonas, 10, Korpus 1, kv. 26, all of Riga, U.S.S.R.

[22] Filed: Aug. 13, 1974

[21] Appl. No.: 496,994

[52] U.S. Cl. .................... 128/2 R; 23/230 B
[51] Int. Cl.² ................................ A61B 5/00
[58] Field of Search ............ 128/2 R, 2 B, 2 A; 23/230 B; 424/2, 3

[56] References Cited
UNITED STATES PATENTS

| | | | |
|---|---|---|---|
| 3,315,229 | 4/1967 | Smithline | 128/2 A X |
| 3,476,514 | 11/1969 | Roth | 23/230 B |
| 3,515,516 | 6/1970 | Horton | 424/3 X |
| 3,690,310 | 9/1972 | Mintz | 128/2 R |
| 3,856,930 | 12/1974 | Nodine et al | 23/230 B X |

OTHER PUBLICATIONS

Excerpta Medica, Cancer, Sec. 16, Vol. 16, No. 12, Dec., 1968, Abstract No. 7119, p. 1126, RC 261.A1E9.

Primary Examiner—Kyle L. Howell
Attorney, Agent, or Firm—Holman & Stern

[57] ABSTRACT

A method of cytological diagnostication of precancer and cancer, which comprises obtaining cytological preparations containing cells suspected of pathology, isolating cells containing nucleoli from among the suspect cells of said preparations, classifying the cells thus selected by the number and size of the nucleoli contained therein, and diagnosing precancer or cancer by the combination of various nucleolar properties.

10 Claims, 16 Drawing Figures

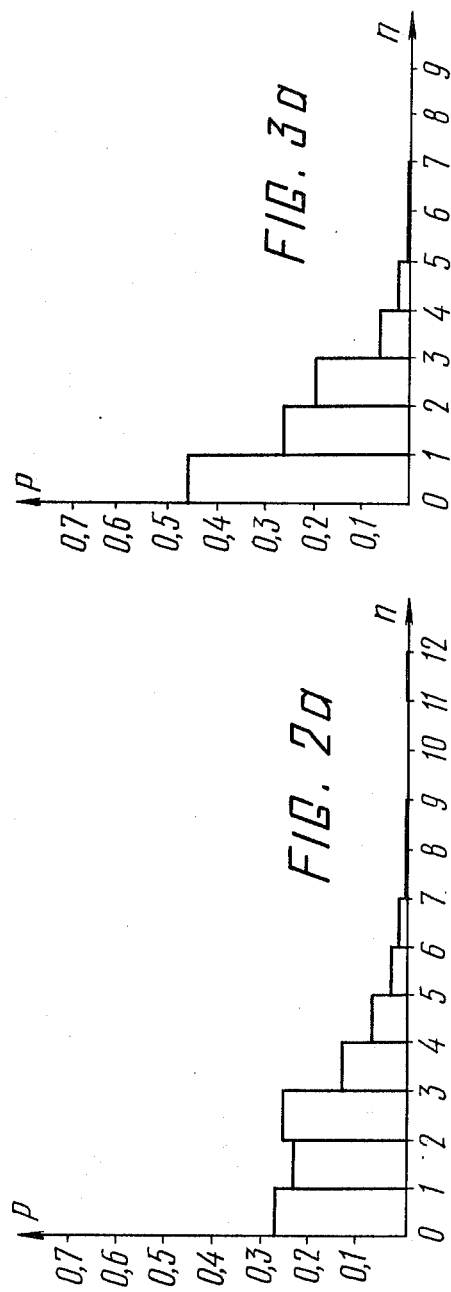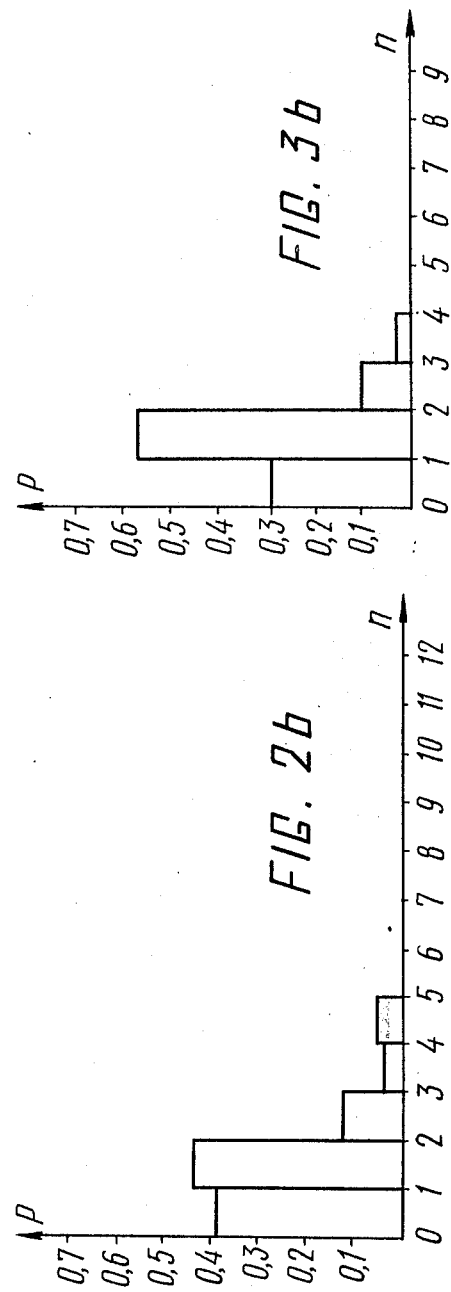

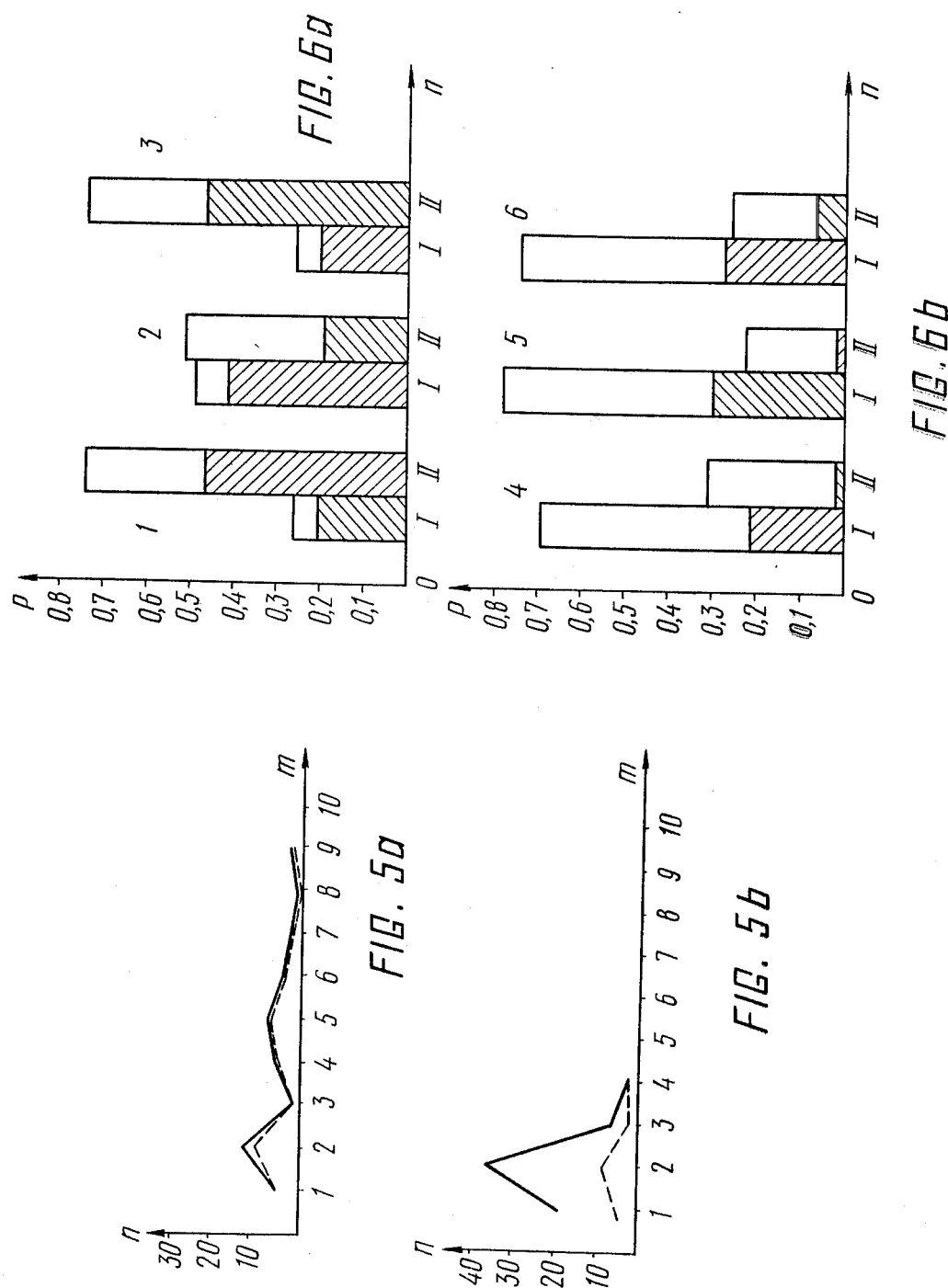

METHOD OF CYTOLOGICAL DIAGNOSTICATION OF PRECANCER AND CANCER

BACKGROUND OF THE INVENTION

The present invention relates to the field of medicine and, more particularly, to methods of cytological diagnosis of precancer and cancer using cytomorphological procedures. The method of the present invention may be employed by clinical research, and preventive medical institutions to study cytological preparations suspected of pathology.

The method of this invention may be employed to diagnose, by nucleolar properties, cytological material prepared and obtained from surgical biopsies, body fluid smears, vaginal smears, exudates and pathological secretions which are fixed and stained so that the nucleoli in the interphase nucleus may be distinguished.

DESCRIPTION OF THE PRIOR ART

It is known in the art to detect cancel cells by a method which comprises measuring the following parameters:

a. the ratio of the nuclear area to the area of the respective cells;

b. the nuclear optical density; and c. the DNA and RNA levels in the cell see U.S. Pat. No. 3,327,119 (well-known Papanicolaou technique).

This known procedure, however, features some disadvantages, such as the need for sophisticated measuring equipment, the inability of distinguishing between precancer and cancer with any adequate degree of reliability (that is to say, the impossibility of performing a differential diagnosis), as well as its inapplicability in cytological laboratories having no sophisticated instrumentation.

SUMMARY OF THE INVENTION

It is an object of the present invention, therefore, to provide a highly accurate method for the differential cytological diagnosis of precancer and cancer.

It is another object of the present invention to provide a method for the differential diagnosis of precancer and cancer requiring no sophisticated measuring instrumentation.

It is still another object of the present invention to provide a simplified procedure for the differential diagnosis of precancer and cancer using nucleolar properties.

It is yet another object of the invention to provide a simplified procedure for the differential diagnosis of precancer and cancer using different quantitative ratios of cells containing nucleoli.

It is a further object of the present invention to provide a simplified procedure for the differential diagnosis of precancer and cancer using different quantitative ratios of cells with larger-diameter nucleoli.

It is one more object of the present invention to provide a simplified procedure for the differential diagnosis of precancer and cancer using generalized nucleolar properties, ratios and various combinations thereof.

These and other objects are attained by providing a method for the cytological diagnosis of precancer and cancer, which comprises first obtaining cytological preparations containing cells suspected of being atypical, isolating from among the suspect cells of said preparations those which contain nucleoli, and classifying the cells thus isolated by the number of nucleoli they contain, after which precancer or cancer is diagnosed by the ratio of cells containing different quantities of nucleoli.

Should the ratio of cells containing more than two nucleoli to those containing one or two cells be less than unity, the cells of the preparation under study are diagnosed as cancerous; whereas should said ratio be more than unity, precancer is diagnosed.

The foregoing objects are also attained by the fact that a method of cytological diagnosis of precancer and cancer is provided, which comprises obtaining cytological preparations whereof the cells are suspected of cancerous or precancerous pathology; isolating from among the suspect cells of said preparations those which contain nucleoli, and isolating therefrom those cells whereof the nucleoli are greater than 2 mcm in diameter, whereupon precancer or cancer is diagnosed by the ratio of the cells containing nucleoli greater than 2 mcm in diameter to the total number of cells containing nucleoli.

Should said ratio be more than 0.6 but less than unity, the cells of the preparation under study are preferably diagnosed as cancerous; whereas should said ratio be less than 0.6, the preferable diagnosis is precancer.

The foregoing objects are likewise attained by the fact that a method of cytological diagnosis of precancer and cancer is provided, which comprises obtaining cytological preparations whereof the cells are suspected of being atypical; isolating from among the suspect cells of said preparations those cells which contain nucleoli, and isolating those cells whereof the nucleoli are equal to, or greater than 2 mcm in diameter, whereupon the cells thus isolated are classified by the number of nucleoli they contain, as well as by the diameters of the nucleoli, and precancer or cancer is diagnosed by the difference in these quantities.

For the "stomach," "cervix uteri" and "lung" localizations, it is possible to determine said difference between the number of cells containing one or two nucleoli smaller than, or equal to 2 mcm in diameter and the number of cells containing one or two nucleoli of which at least one exceeds 2 mcm in diameter; another said difference is determined between the number of cells containing one or two nucleoli smaller than, or equal to 2 mcm in diameter, and the number of cells containing more than two nucleoli of which at least one exceeds 2 mcm in diameter, and should both said differences be negative, the preparation in question is diagnosed as cancerous; whereas should both said differences be positive, the preparation in question is diagnosed as precancerous.

BRIEF DESCRIPTION OF THE TABLES AND DRAWINGS

The proposed method of cytological diagnosis of precancer and cancer will be better understood from the following detailed description of some specific applications thereof taken in conjunction with the accompanying drawings and with reference to the accompanying tables, wherein:

Table 1 presents the number of cells with nucleoli in the cytological preparations of cancer and precancer of the stomach, the cervix uteri and the lungs, in accordance with the invention;

Table 2 presents combinations of nulceolar properties for diagnosing cytological preparations, in accordance with the invention;

Tables 3a, b and c present diagnosis reliability estimates, in accordance with the invention:
a. for 20 atypical cells;
b. for 40 atypical cells; and
c. for two-stage diagnosis by 20 and 40 cells;

Table 4 presents the results of diagnosis of precancer and cancer of the stomach by $\Delta_1$; $\Delta_2$; $K_1$ and $K_2$, in accordance with the invention;

Table 5 presents the results of diagnosis of precancer and cancer of the cervix uteri and the lungs by $\Delta_1$ and $\Delta_2$, in accordance with the invention;

FIG. 2 is the distribution of atypical cells with a specified number of nucleoli, in accordance with the invention:
a. in cytological preparations of cancer of the cervix uteri; and
b. in cytological preparations of precancer of the cervix uteri;

FIG. 3 is the distribution of atypical cells with a specified number of nucleoli, in accordance with the invention:
a. in cytological preparations of lung cancer patients; and
b. in cytological preparations of lung precancer patients;

Figure 7:
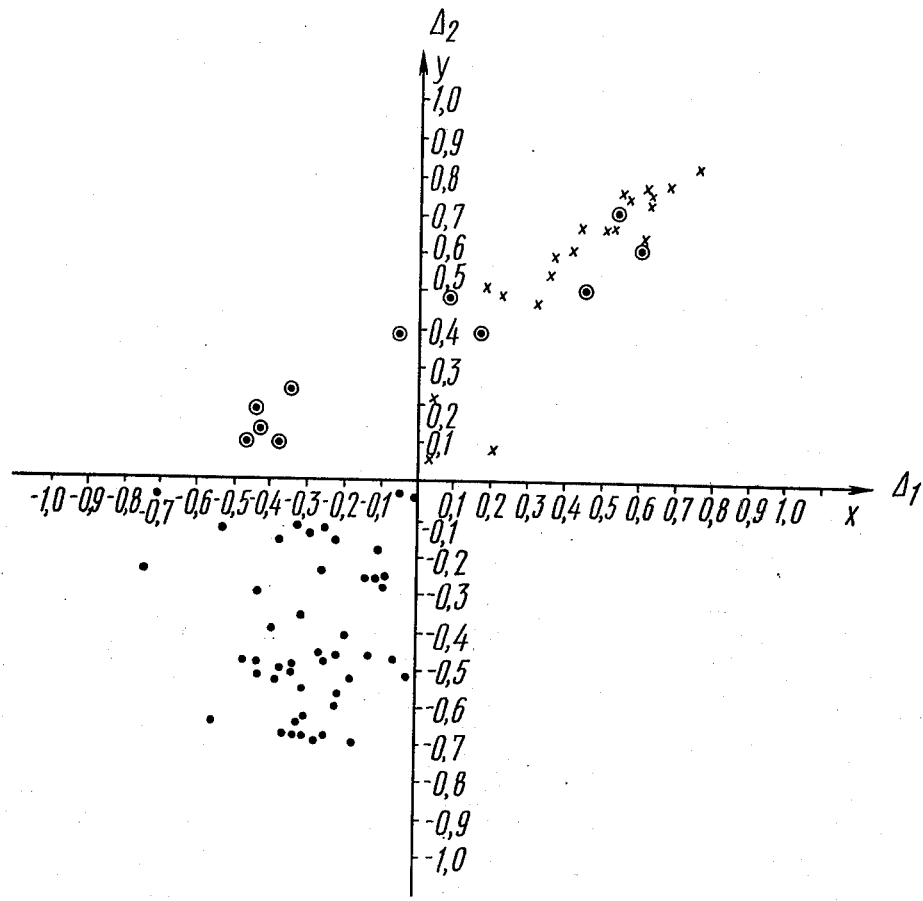
Figure 8:
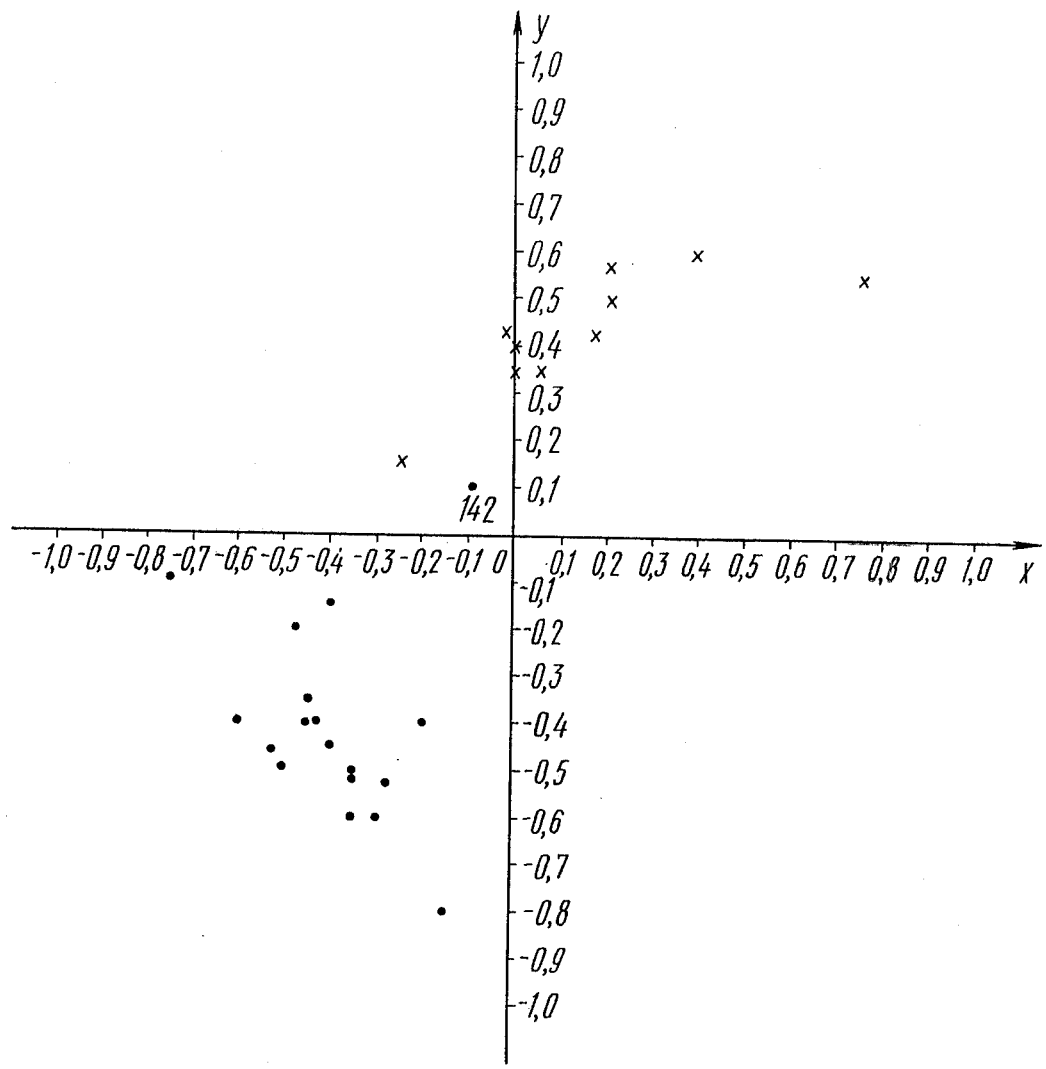
Figure 9:
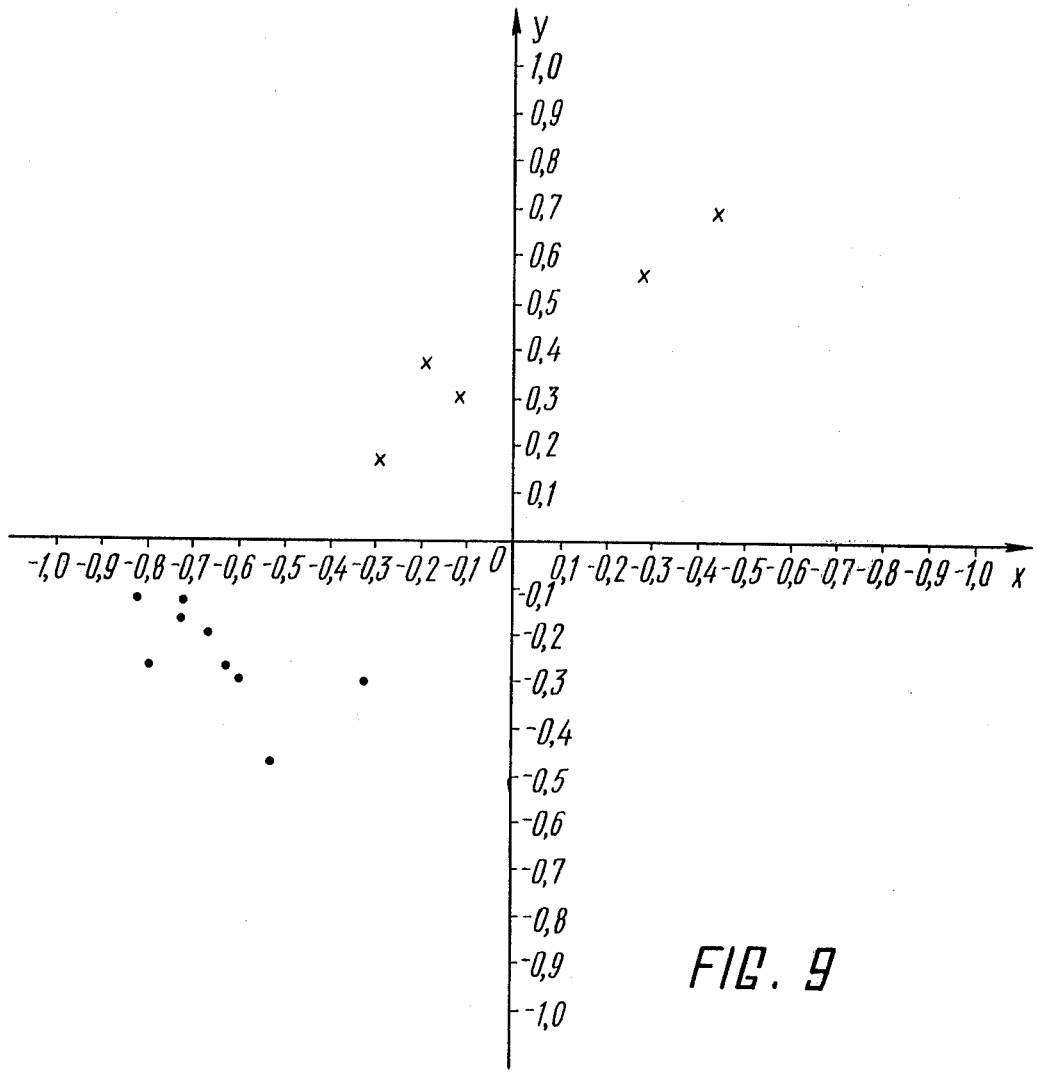
Figure 10:
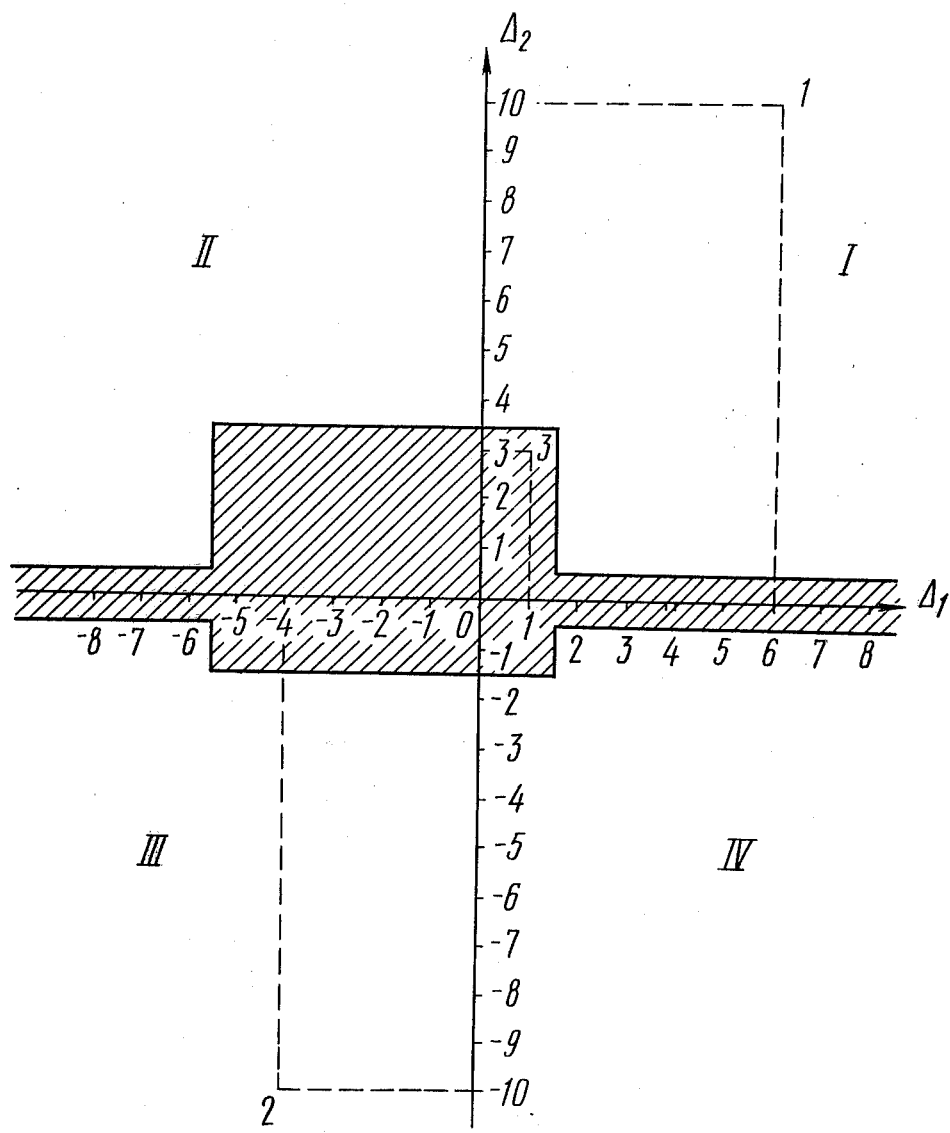

FIG. 5 presents the number of atypical cells containing larger-diameter nucleoli in cytological preparations, in accordance with the invention:
a. cancer cases; and
b. precancer cases;

FIG. 6 presents the number of larger-diameter nucleoli against the total number of nucleoli, in accordance with the invention:
a. in cytological preparations taken from patients suffering from cancer of: the cervix uteri - 1; the lungs - 2; and the stomach - 3; and
b. in cytological preparations taken from patients suffering from precancer of: the cervix uteri - 4; the lungs - 5; and the stomach - 6;

FIG. 7 illustrates the diagnosis of cytological preparations of cancer and precancer of the stomach, in accordance with the invention;

FIG. 8 illustrates the diagnosis of cytological preparations of precancer of the cervix uteri, in accordance with the invention;

FIG. 9 illustrates the diagnosis of cytological preparations of precancer of the lungs, in accordance with the invention; and FIG. 10 illustrates the diagnosis of cytological preparations of precancer and cancer (marginal cases), in accordance with the invention.

The reduction of a huge body of statistical material on the preparations obtained from patients suffering from precancer or cancer of the stomach, precancer or cancer of the cervix uteri and precancer or cancer of the lungs (the total number of studied cells exceeded 20,000) revealed that no less than 95 percent of the pathologically altered cells in the cancer preparations, and no less than 60 percent of pathologically altered cells in the precancer preparations contained nucleoli.

Table 1 presents some sample results of studies of the preparations of pathologically altered cells of cancer and precancer of the stomach, cancer and precancer of the cervix uteri, and cancer and precancer of the lungs. As can be seen in the table, the number of pathological cells containing nucleoli significantly, and in some cases (cancer of the stomach, lung and cervix uteri) considerably, exceeds the number of cells containing no nucleoli. Thus, for instance, for cancer of the stomach, of the total 2,450 cells in 20 preparations from 17 patients, 95 percent do contain nucleoli. For precancer of the stomach, the corresponding proportion is 70 percent. These proportions of cells containing nucleoli, and those containing no nucleoli were found to be practically sufficient to establish a diagnosis by nucleolar properties. It can be seen in Table 1 that the situation is similar for cancer and precancer of the lungs and cancer and precancer of the cervix uteri.

However, the mere fact that cells with nucleoli are there is not nearly enough for the purposes of differential diagnosis. Hence, in accordance with the invention, another parameter is taken into account, viz. distribution of cells with a predetermined number of nucleoli. Such a distribution is shown in FIG. 1a for cancer and precancer of the stomach, in FIG. 2 for cancer and precancer of the cervix uteri and in FIG. 3 for cancer and precancer of the lungs.

Figure 1A:
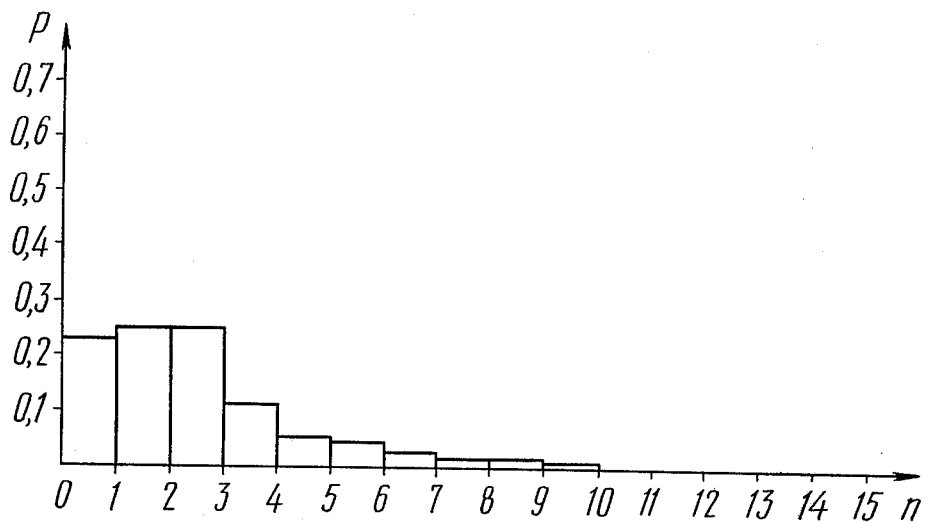
FIG. 1 is the distribution of atypical cells containing a specified number of nucleoli, in accordance with the invention:
a. in cytological preparations of cancer of the stomach; and
b. in cytological preparations of precancer of the stomach.
Figure 1B:
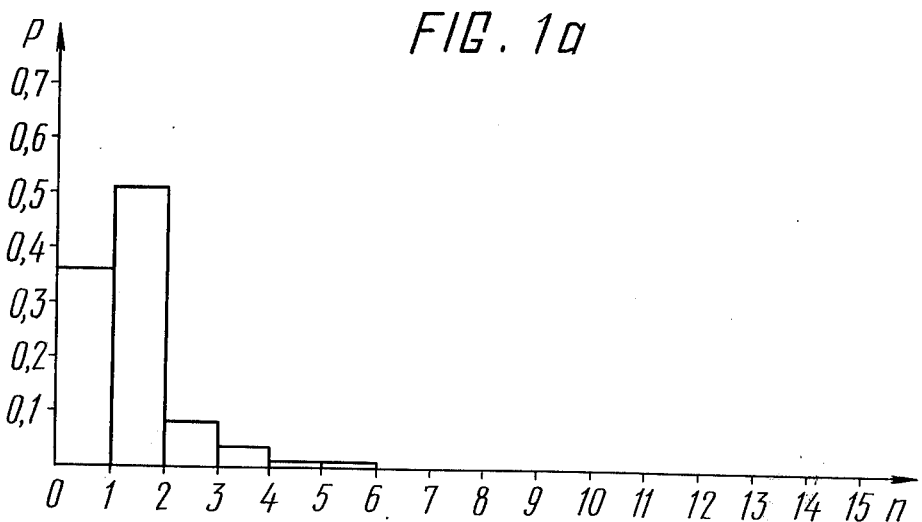

In FIGS. 1a and 1b, on the abscissa the number of cells $n$ is plotted containing a predetermined number of nucleoli, while on the ordinate their relatively frequency $p$ is plotted.

Figure 4B:
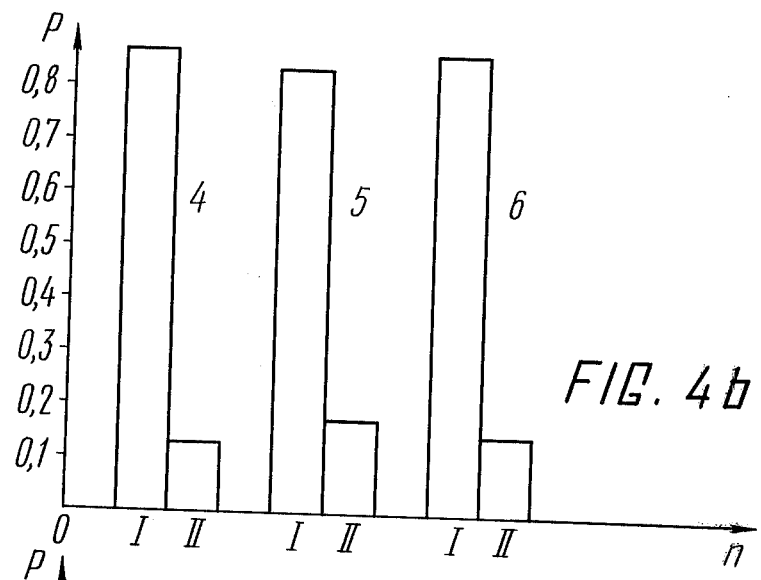
FIG. 4 is the distribution of the number of nucleoli by Groups 1 and 2, in accordance with the invention:
a. cancer of the stomach - 4; cancer of the cervix uteri - 5; and cancer of the lungs - 6;
b. precancer of the stomach - 1; precancer of the cervix uteri - 2; and precancer of the lungs - 3.
Figure 4A:
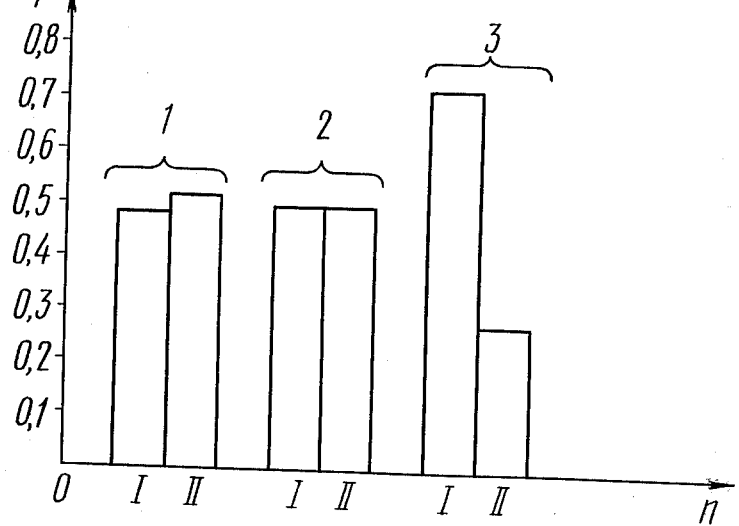

The cancer preparations of FIG. 1a (the histogram is plotted from 2,529 cells) contain a great number of cells with an increased (up to 10) number of nucleoli. In FIG. 1b based on 1,458 cells, there is a preponderance of cells containing one or two nucleoli. This means that for practical differential diagnosis, the following criterion may be employed: to consider the distribution of cells containing one or two nucleoli, and the distribution of cells containing three and more nucleoli. A similar pattern of distribution of cells containing nucleoli is observed in FIGS. 2a and 2b (440 and 360 cells, respectively) - cancer and precancer of the cervix uteri, as well as in FIGS. 3a and 3b (270 and 150 cells, respectively) - cancer and precancer of the lungs. This kind of distribution is illustrated most graphically in FIGS. 4a and 4b. In the histogram of FIG. 4a, the pathological cells of cancer of the stomach 1, cervix uteri 2 and lungs 3, containing nucleoli, are distributed into two groups, I and II. Group I of each localization includes cells with one or two nucleoli, whereas Group II includes cells containing three or more nucleoli.

The pathological cells of precancer of the stomach 4, cervix uteri 5 and lungs 6 are similarly distributed into two groups.

The pattern of distribution of the relative frequencies of the number of nucleoli in Groups I and II bears out the earlier conclusion that precancer is characterized by an increase in the number of pathological cells containing one or two nucleoli, while cancer preparations are characterized by a reduction the number of cells containing one or two nucleoli, and an increase in the number of cells with three or more nucleoli.

In the light of the foregoing clarifications, the proposed method consists in the following:

Preparations whose cells are suspected of precancer or cancer are obtained by any known method.

DESCRIPTION OF THE PREFERRED EMBODIMENTS

Then cells containing nucleoli are isolated from the preparations taken from suspected precancer and cancer cases. The nucleous-containing cells may be isolated under a microscope with at least a 90 × 7 magnification, and with the use of an oil immersion lens by the following morphological features:

a. altered cell shape;
b. altered nuclear-cytoplasmic ratio.

The altered cell shape implies various deviations of the cell shape from all possible shape varieties of the normal cell inherent in a given tissue and category of cells, whereas the altered nuclear-cytoplasmic ratio is one greater than 0.3, and corresponding to cases where the nucleous occupies approximately ⅓ of the cytoplasm.

While developing and testing the proposed method it was found that only about 100 cells containing nucleoli were sufficient for the purposes of differential diagnosis of precancer and cancer. However, this number may be greatly reduced depending on the particular localization, and the specific type of benign or malignant process. Furthermore, the number of cells required to establish a diagnosis is reduced still more if additional nucleolar parameters are taken into account.

Further, in accordance with the invention, the isolated cells are distributed by the number of nucleuli they contain. To this end, as has been shown above, the nucleoli in each cell are counted, and all cells are broken down into two groups.

Group I includes cells with one or two nucleoli, and Group II cells containing three or more nucleoli. After the grouping, the ratio of the number of cells with one or two nucleoli to the number of cells with three or more nucleoli, that is to say the ratio $K_1$, is determined.

With the ratio $K_I$ smaller than or equal to unity, the preparation is diagnosed as cancerous; with a $K_I$ ratio greater than unity the preparation is regarded as indicative of precancer.

In addition, studies of the cytological material of precancer and cancer patients revealed that, not only did pathological cells contain a different number of nucleoli, but that the size or volume of the nucleoli themselves was likewise different. In order to evaluate these changes, the pathological cells are divided into two groups, one including cells with nucleoli smaller than or equal to 2 mcm in diameter, and the other whose cells have a diameter greater than 2 mcm. Said limit of 2 mcm was chosen on the basis of studies of normal cell nucleoli which never exceed 2 mcm in diameter.

In FIG. 5a, the solid line represents the distribution of the total number $u$ of nucleolus-containing cells in cancer preparations, while the dotted line illustrates the distribution of cells with larger-diameter nucleoli. The two curves almost merge, indicating the abundance of cells with larger-diameter nucleoli in the cancer preparations.

As regards precancer preparations, however, it will be seen in FIG. 5b that, as shown by the distribution of normalvolume cells with nucleoli (solid line), and that of cells containing nucleoli of increased volume (dotted line), the number of pathological cells containing larger-diameter nucleoli is small as compared with the overall number of cells with nucleoli. Hence, one way of diagnosing precancer and cancer preparations is by the ratio of the member of pathologically altered cells with nucleoli to the number of pathologically altered cells containing larger-diameter nucleoli. In accordance with the invention, the cells with nucleoli exceeding 2 mcm in diameter are isolated from the population of pathologically altered cells with nucleoli, and the ratio $K_2$ of the cells containing larger-diameter cells nucleoli to the overall number of cells containing nucleoli is determined.

If the $K_2$ ratio is within $0.6 < K_2 < 1$, then cancer is diagnosed; if $K_2 > 0.6$, then precancer is diagnosed.

In both figures, the abscissa is the number of nucleoli in the cell, $m$, and the ordinate is the overall number of cells, $n$.

FIGS. 6a and 6b illustrate the distribution of larger-diameter nucleoli (hatched area) in the population of nucleoli in Groups I and II of pathologically altered cells distributed by the number of nucleoli with the view of studying the quantitative nucleolus ratios $K_1$.

In the pathologically altered cells with nucleoli of Groups I and II the following forms of pathology were diagnosed: cancer of the stomach - 1, cancer of the cervix uteri - 2, cancer of the lungs - 3; precancer of the stomach - 4; precancer of the cervix uteri - 5, and precancer of the lungs - 6. The histograms of FIGS. 5a and 5b are plotted by the same number of cells of the same patients as those used in FIGS. 1 to 4. As can be seen in FIG. 6a, in the cells of Groups I of cancer cases 1, 2 and 3, the larger-diameter nucleoli account for over half of the total number of nucleoli. In the cancer cells of Groups II, excepting cancer of the lung, over half of the total number of cells are those which contain larger-diameter nucleoli. In the cells of Groups I (FIG. 5b) of precancer cases 4, 5 and 6, the larger-diameter nucleoli account for far less than half of the total, particularly in the cells of Groups II.

In this case, too, the $K_2$ ratio may be employed to diagnose precancer and cancer.

While developing and testing the proposed method, it was found that reliable diagnosis using the $K_1$ or $K_2$ ratios called for a considerable number of pathologically altered cells in cancer and precancer preparations, which adversely affects the diagnostic time, and prevents the method from being widely applied in clinical practice.

The results of investigations relating to Table 2 were the population of precancer and cancer cells may be broken then into four groups containing nucleoli. The table is made up of four columns:

1. combinations of features;
2. number of cells with one or two nucleoli;
3. number of cells with more than two nucleoli; and
4. number of cells with larger-diameter nucleoli (even if the cell contains but one nucleolus).

The cytologist studying each pathologically altered cell with a nucleolus must determine whether or not the cell features a given property. For the practical purposes of cytological diagnosis of precancer and cancer, the following generalized nucleolar properties are used:

A - one or two nucleoli, the nucleoli being normal in diameter;
B - one or two nucleoli, with at least one of them having an increased diameter;

C – the nucleoli are three or more in number with at least one having an increased diameter.

Each pathologically altered cell with a nucleolus can exhibit only one of these properties (either A, or B, or C). If a certain number of pathological cells with $n$ nucleoli are isolated from a cytological preparation, then $X_{i(n)}$ will denote the presence of the i-th property in these cells. Investigations indicate that with a sufficient number of pathologically altered cells the following relationships emerge: into precancer:

$$X_{A(n)} > X_{B(n)} \text{ and } X_{A(n)} > X_{C(n)},$$

that is the number of cells featuring the property A is greater than the number of cells with the properties B and C; and cancer:

$$X_{A(n)} < X_{B(n)} \text{ and } X_{A(n)} < X_{C(n)},$$

that is the number of cells featuring the property A is less than the number of cells with the properties B and C.

For practical diagnostics, in accordance with the invention, the isolated pathological cells (isolation is carried out in the same way as in the above-described procedures) are classified by the A, B and C properties.

The most convenient way of using the foregoing relationships for practical diagnostics is to express them by differences, since studies into the properties of these characteristics conducted on preparations having varified diagnoses show that the optimum diagnostic method ensuring a very high level of accuracy, and requiring no complex calculations (i.e. division needed to calculate the relationships) must use the difference:

$$\Delta_1 = X_{A(n)} - X_{B(n)}, \text{ i.e.}$$

for a given number of cells, it is necessary first to count the number of cells featuring the A property and the number of cells exhibiting the B property, and then to subtract the latter from the former, and $$\Delta_2 = X_{A(n)} - X_{C(n)}, \text{ i.e.}$$

for a given number of cells chosen to calculate both $\Delta_1$ and $\Delta_2$, it is necessary to count the number of cells featuring the C property, and subtract it from the number of cells with the A property.

Calculation of such differences is likewise convenient when realizing simple diagnostic devices. If complex calculations can be dispensed with, then use can be made of the following relationships:

$$K_3 = \frac{X_{A(n)}}{X_{B(n)}} \text{ and } K_4 = \frac{X_{A(n)}}{X_{C(n)}}.$$

where $K_3$ is the ratio of pathologically altered cells containing one or two nucleoli of diameter smaller than or equal to 2 mcm to those containing one or two nucleoli of which at least one has a diameter of over 2 mcm, whereas $K_4$ is the ratio of cells with one or two nucleoli of diameter smaller than or equal to 2 mcm to those containing more than two nucleoli of which at least one has a diameter of over 2 mcm.

Thus, in accordance with the invention, the isolated pathological cells containing nucleoli are distributed by the A, B and C properties, with the differences $\Delta_1$ and $\Delta_2$ being determined. If the differences $\Delta_1$ and $\Delta_2$ are negative in value, then the preparations are classified as cancerous; and if the differences $\Delta_1$ and $\Delta_2$ are positive, then the preparation is classified as precancerous. However, the preparation may be diagnosed as precancerous, if the difference $\Delta_2$ is positive but $\Delta_1$ is negative. Using these values of $\Delta_1$ and $\Delta_2$ for precancer of the stomach, it is possible to diagnose healing gastric ulcer which can hardly be diagnosed otherwise.

In order to clarify the combined diagnostic value of the $\Delta_1$ and $\Delta_2$ characteristics the following geometric illustration will be employed: Each preparation may be denoted by a point in a two-dimensional orthogonal Cartesian system of coordinates., also bearing in mind that the coordinate axes divide the plane into four parts – squares I, II, III and IV.

Should it become necessary to compare $\Delta_1(n)$ and $\Delta_2(n)$ calculated for different preparations containing different numbers of cells, relative quantities are to be used:

$$\Delta_1 = \frac{\Delta_1(n)}{n} \text{ and } \Delta_2 = \frac{\Delta_2(n)}{n},$$

where $n$ is the total number of cells studied.

The values of these quantities will lie between $-1$ and $+1$.

The $\Delta_1 = X_{A(n)} - X_{B(n)}$ property will be plotted on the abscissa of the graphs of FIGS. 7, 8 and p, while the $\Delta_2 = X_{A(n)} - X_{C(n)}$ property will be plotted on the ordinate. The calculated values of $\Delta_1$ and $\Delta_2$ for a precancerous or cancerous preparation will be denoted by points falling within a particular square I, II, III or IV of the coordinate system.

The point corresponding to precancerous preparations is designated by a cross (+), the point corresponding to cancer by a dot (.), and the point corresponding to proliferative process (e.g. healing gastric ulcer) by an encircled dot ( ).

FIG. 7 presents an example of diagnostication of gastric cancer and precancer preparations, where the cancer preparations characterized by negative $\Delta_1$ and $\Delta_2$ fall within the square III, with the precancer preparations with positive $\Delta_2$ and negative or positive $\Delta_1$ falling within the squares I and II, and the preparations with positive $\Delta_2$ and negative $\Delta_1$ being characteristic of the proliferative processes (e.g. healing gastric ulcer). So, the proposed method allows for diagnosing the healing of a gastric ulcer which normally poses enormous diagnostic difficulties.

FIGS. 8 and 9 present examples of diagnostication of precancer and cancer of the cervix uteri and the lungs. In this case, too, the points corresponding to the cancer preparations with negative $\Delta_1$ and $\Delta_2$ fall within the square III, and the points corresponding to the precancer preparations with positive $\Delta_2$ and positive or negative $\Delta_1$ fall within the squares I and II.

Reliable diagnostication using the $\Delta_1$ and $\Delta_2$ differences is possible, provided that the preparation comprises 100 or more pathologically altered cells containing nucleoli. This requirement, however, adds to the labor input in the search for and analysis of pathologically altered cells in the preparation. Yet, it was found that most preparations could be reliably diagnozed by as few as 20 or even less isolated pathological cells. For this reason, a sequential procedure with fixed samples is used. Experience shows the expedience of using three fixed samples: 20, 40 and 60 cells. First, 20 pathologically altered cells are sampled, then the $\Delta_1$ and $\Delta_2$ differences are calculated, and a diagnosis is established.

FIG. 10 is an orthogonal cartesian system of coordinates with a hatched area representing a region of unreliable or marginal diagnoses which was delimited on the basis of the cytological material of gastric precancer and cancer with verified diagnoses. In the course of the diagnostic process, as the number of preparations increases, the limits of the marginal region can be further refined.

Should a point with the coordinates $\Delta_1$ and $\Delta_2$ fall within the marginal region, the number of cells is to be raised to 40. The diagnostic process is repeated, and should the point in question again fall within the marginal region, the cell number is again raised by 20, or else more reliable cytological material is necessary.

However, the actual values of probability of error indicate a high level of diagnostic reliability, with the proportion of marginal diagnoses in a two-stage procedure (that is to say by 40 cells) being only 5 percent. As shown by investigations, the use of other nucleolar, or dimensional and structural properties permits cutting down the requisite number of pathologically altered cells without interfering with the reliability of diagnosis. Thus, in order to diagnose cancer of the stomach, as few as 7 cells are required.

Many cytological laboratories have been conducting clinical trials of the proposed method of differential cytological diagnosis of precancer and cancer by nucleolar properties. Since the proposed method is compatible with all the staining compounds which permit discerning the structure of the cell and the nucleus, i.e. which show the structure of the nucleoli so that they can be identified, counted and their diameter measured by indirect methods, it may be instrumental in evaluating even those precancer and cancer suspected preparations which are delivered to cytological laboratories from screening centers. Thus, preparations can be studied which are selected by automatic early diagnosis systems charged with the task of identifying preparations suspected of being cancerous.

Since the suspect preparations and the cells sampled in fixed amounts (20, 40, etc.) exhibit a certain combination of generalized nucleolar properties A, B and C, all diagnoses can be comparatively evaluated by the $K_1$ and $K_2$ ratios as well as by the differences $\Delta_1$ and $\Delta_2$.

The optimal and most reliable diagnostic procedure is one based on the combined $\Delta_1$ and $\Delta_2$ properties, which is the reason why diagnosis reliability estimates for precancer and cancer of the stomach are presented hereinbelow.

Tables 3a, 3b and 3c give diagnostic reliability estimates for gastric diseases, where $\alpha$ is the probability of diagnosing a precancer preparation as cancerous, $\beta$ is the probability of diagnosing a cancer preparation as precancerous $\gamma_1$ is the probability of unreliable, or marginal diagnosis of a cancer preparation, and $\gamma_2$ is the probability of unreliable or marginal diagnosis of a precancer preparation. The probability of marginal diagnosis of any preparation is $\gamma$. The values of these quantities characterize the quality of diagnosis for 20 pathological cells in Table 3a, for the 40 cells in Table 3b, and for a two-stage procedure by 20 and then 40 cells in Table 3c. Upon analysis of these results, it is necessary to remember that they represent the upper estimates of the corresponding probabilities. Thus, the probabilities of error, and of marginal diagnosis were separately estimated for each difference $\Delta_1$ and $\Delta_2$. As can be seen in Table 3c, in a two-stage diagnostic procedure, the proportion of marginal diagnoses is very low (<5 percent).

Table 4 presents a sample of a diagnoses of 25 gastric cancer preparations, and 16 gastric precancer preparations using the differences $\Delta_1$ and $\Delta_2$ and the ratios $K_1$ and $K_2$.

Table 5 presents a sample of a diagnoses of 5 lung precancer preparations, and 10 uterine precancer preparations using the differences $\Delta_1$ and $\Delta_2$. A sample of a diagnosis of 10 lung cancer preparations, and 5 uterine cancer preparations is also shown.

At the first stage of verification of the proposed diagnostic method, 120 preparations of precancer and cancer of the stomach, 40 preparations of precancer and cancer of the lungs, and 60 preparations of precancer and cancer of the cervis uteri were analyzed.

All in all, 220 preparations taken from precancer and cancer patients were studied.

The group of marginal diagnoses included 9 preparations, or 4 percent of the total. In 5 cases the precancer preparations were erroneously diagnosed as cancerous, and in 3 cases cancer preparations were erroneously diagnosed as precancerous.

Table 1

| No. | Diagnosis | No. of patients | No. of samples | No. of cells | No. of cells with nucleoli | % |
|---|---|---|---|---|---|---|
| 1. | Gastric cancer | 17 | 20 | 2,450 | 2,332 | 95 |
| 2. | Gastric precancer | 21 | 26 | 2,627 | 1,848 | 70 |
| 3. | Lung cancer | 15 | 15 | 1,500 | 1,485 | 99 |
| 4. | Lung precancer | 15 | 15 | 1,500 | 975 | 65 |
| 5. | Uterine cancer | 15 | 15 | 1,500 | 1,452 | 97 |
| 6. | Uterine precancer | 15 | 15 | 1,500 | 912 | 61 |

Table 2

| Combinations of properties | No. of nucleoli 1–2 | Number of nucleoli more than 2 | Larger-diameter nucleoli |
|---|---|---|---|
| A | + | − | − |
| B | + | − | + |
| C | − | + | − |
| D | − | + | + |

Table 3

| Size | Estimate | Size | Estimate | Size | Estimate |
|---|---|---|---|---|---|
| $\alpha$ (20) | 0.03 | $\alpha$ (40) | 0.03 | $\alpha$ (20,40) | 0.05 |
| $\beta$ (20) | 0.03 | $\beta$ (40) | 0.03 | $\beta$ (20,40) | 0.04 |
| $\gamma_1$(20) | 0.2 | $\gamma_1$(40) | 0.05 | $\gamma_1$(20,40) | 0.05 |
| $\gamma_2$(20) | 0.22 | $\gamma_2$(40) | 0.05 | $\gamma_2$(20,40) | 0.05 |
| $\gamma$ (20) | 0.21 | $\gamma$ (40) | 0.05 | $\gamma$ (20,40) | 0.05 |
| a | | b | | c | |

Table 4

| No. | No of the patient | | | | | No of cells | Diagnosis |
|---|---|---|---|---|---|---|---|
| 1 | 2 | 3 | 4 | 5 | 6 | 7 | 8 |
| 1. | | 26 | −26 | −69 | 0.04 | 0.97 | 100 | Gastric cancer |
| 2. | | 30 | −21 | −16 | 0.50 | 0.79 | 100 | " |
| 3. | | 27 | −12 | −26 | 0.60 | 0.72 | 100 | " |
| 4. | | 36 | −8 | −25 | 0.70 | 0.73 | 100 | " |

Table 4-continued

| No. | No of the patient | | | | | No of cells | Diagnosis |
|---|---|---|---|---|---|---|---|
| 1 | 2 | 3 | 4 | 5 | 6 | 7 | 8 |
| 5. | 116 | −73 | −24 | 0.01 | 0.99 | 100 | " |
| 6. | 108 | −12 | −34 | 0.07 | 0.96 | 50 | " |
| 7. | 91 | −21 | −26 | 0.04 | 0.98 | 50 | " |
| 8. | 93 | −21 | −24 | 0.05 | 0.98 | 50 | " |
| 9. | 29 | −24 | −13 | 0.43 | 0.73 | 100 | " |
| 10. | 40 | −36 | −16 | 0.40 | 0.78 | 100 | " |
| 11. | 92 | −21 | −15 | 0.16 | 0.88 | 50 | " |
| 12. | 94 | −23 | −24 | 0.04 | 0.90 | 50 | " |
| 13. | 37 | −25 | −24 | 0.40 | 0.81 | 100 | " |
| 14. | 41 | −14 | −7 | 0.40 | 0.74 | 50 | " |
| 15. | 38 | −31 | −68 | 0 | 0.99 | 100 | " |
| 16. | 113 | −59 | −135 | 0.01 | 0.98 | 200 | " |
| 17. | 28 | −18 | −41 | 0.30 | 0.89 | 100 | " |
| 18. | 35 | −8 | −29 | 0.70 | 0.73 | 100 | " |
| 19. | 70 | −6 | −17 | 0.25 | 0.96 | 30 | " |
| 20. | 87 | −18 | −25 | 0.10 | 0.96 | 50 | " |
| 21. | 72 | −16 | −34 | 0 | 0.96 | 50 | " |
| 22. | 71 | −35 | −2 | 0.10 | 0.90 | 50 | " |
| 23. | 42 | 61 | 78 | 4.6 | 0.17 | 100 | Gastric precancer |
| 24. | 48 | 35 | 47 | 4.0 | 0.17 | 62 | " |
| 25. | 47 | 37 | 46 | 4.7 | 0.02 | 60 | " |
| 26. | 49 | 31 | 41 | 3.9 | 0.30 | 60 | " |
| 27. | 13 | 6 | 50 | 1.1 | 0.46 | 100 | " |
| 28. | 45 | 24 | 38 | 3.2 | 0.22 | 56 | " |
| 29. | 115 | 9 | 26 | 1.4 | 0.38 | 50 | " |
| 30. | 11 | 35 | 47 | 3.8 | 0.10 | 70 | " |
| 31. | 55 | 7 | 46 | 1.1 | 0.37 | 100 | " |
| 32. | 54 | 17 | 54 | 1.4 | 0.39 | 100 | " |
| 33. | 57 | 34 | 48 | 2.4 | 0.32 | 100 | " |
| 34. | 118 | 13 | 24 | 1.9 | 0.36 | 49 | " |
| 35. | 51 | 16 | 37 | 1.4 | 0.39 | 100 | " |
| 36. | 101 | 35 | 55 | 2.5 | 0.27 | 100 | " |
| 41. | 148 | 33 | 15 | 2.6 | 0.35 | 159 | " |

Table 5

| No. | No of the patient | | | No of cells | Diagnosis |
|---|---|---|---|---|---|
| 1 | 2 | 3 | 4 | 5 | 6 |
| 1. | 24 | +4 | +9 | 30 | Lung precancer |
| 2. | 21 | +13 | +21 | 30 | " |
| 3. | 20 | +6 | +11 | 30 | " |
| 4. | 22 | +9 | +5 | 30 | " |
| 5. | 23 | +8 | +15 | 30 | " |
| 6. | 16 | +22 | −4 | 30 | Lung cancer |
| 7. | 15 | −20 | −6 | 30 | " |
| 8. | 14 | −10 | −9 | 30 | " |
| 9. | 68 | −16 | −14 | 30 | " |
| 10. | 34 | −25 | −4 | 30 | " |
| 11. | 67 | −19 | −5 | 30 | " |
| 12. | 17 | −24 | −5 | 30 | " |
| 13. | 18 | −18 | −1 | 30 | " |
| 14. | 19 | −22 | −5 | 30 | " |
| 15. | 139 | 0 | 7 | 20 | Uterine precancer |
| 16. | 140 | 15 | 11 | 20 | " |
| 17. | 141 | 1 | 7 | 20 | " |
| 18. | 137 | 0 | 8 | 20 | " |
| 19. | 7 | 6 | 15 | 30 | " |
| 20. | 6 | 1 | 13 | 30 | " |
| 21. | 138 | 5 | 3 | 20 | " |
| 22. | 11 | 39 | 60 | 100 | " |
| 23. | 8 | 6 | 17 | 30 | " |
| 24. | 9 | 5 | 13 | 30 | " |
| 25. | 3 | −9 | −18 | 30 | Uterine cancer |
| 26. | 128 | −8 | −3 | 20 | " |
| 27. | 132 | −7 | −12 | 20 | " |
| 28. | 129 | −12 | −8 | 20 | " |
| 29. | 127 | −9 | −7 | 20 | " |
| 30. | 135 | −8 | −9 | 20 | " |

What we claim is:

1. A method of cytological diagnosis of precancer and cancer, comprising obtaining cytological preparations containing cells suspected of being atypical, isolating from among the suspect cells of said preparations those cells which contain nucleoli; classifying the cells thus isolated by the number of nucleoli contained therein; and determining the ratio of the number of cells containing greater than two nucleoli to the number of those containing one or two nucleoli; and, should said ratio be less than unity, the preparation under study is diagnosed as cancerous, whereas should said ratio be greater than unity, the preparation under study is diagnosed as precancerous.

2. A method of cytological diagnosis of precancer and cancer, comprising obtaining cytological preparations containing cells suspected of being atypical, isolating from among the suspect cells of said preparations those cells which contain nucleoli; and isolating therefrom those cells whereof the nucleoli have greater than 2 mcm in diameter; determining the ratio of the cells containing nucleoli greater than 2 mcm in diameter to the total number of all cells containing nucleoli; and, should said ratio be greater than 0.6 but less than unity, the preparation under study is diagnosed as cancerous, whereas should said ratio be less than 0.6, the preparation under study is diagnosed as precancerous.

3. A method of cytological diagnosis of precancer and cancer, which comprises obtaining cytological preparations containing cells suspected of being atypical: isolating from among the suspect cells of said preparations those cells which contain nucleoli, and isolating therefrom those cells which contain nucleoli equal to 2 mcm in diameter; classifying the cells thus isolated by the number of nucleoli contained therein, as well as by the diameters of said nucleoli; determining the difference between said cells, and, for the stomach, cervix uteri and lung localizations, said difference is determined between the number of cells containing one or two nucleoli whereof at least one has a diameter greater than 2 mcm, while another said difference is determined between the number of cells containing one or two nucleoli smaller than 2 mcm in diameter and the number of cells containing greater than two nucleoli, and, should both said differences be negative in value, the preparation under study is diagnosed as cancerous, while should both said differences be positive in value, the preparation under study is diagnosed as precancerous.

4. A method of cytological diagnosis of precancer and cancer, which comprises obtaining cytological preparations containing cells suspected of being atypical; isolating from among the suspect cells of said preparations those cells which contain nucleoli, and isolating therefrom those cells whereof the nucleoli are equal to 2 mcm in diameter; distributing the cells thus isolated by the number of nucleoli contained therein as well as by the diameters of said nucleoli; determining the difference between said cells, and, for the stomach, cervix uteri and lung localizations, said difference is determined between the number of cells containing one or two nucleoli wheof at least one is greater than 2 mcm in diameter, whereas another said difference is determined between the number of cells containing one or two nucleoli equal to 2 mcm in diameter, and the number of cells containing more than two nucleoli whereof at least one is greater than 2 mcm in diameter, and, should both said differences be negative in value, the preparation under study is diagnosed as cancerous, while should both said differences be positive in value, the preparation under study is diagnosed as precancerous.

5. A method of cytological diagnosis of precancer and cancer, which comprises obtaining cytological preparations containing cells suspected of being atypical; isolating from among the suspect cells of said preparations those which contain nucleoli, and isolating therefrom those cells whereof the nucleoli are greater than 2 mcm in diameter; classifying the cells thus isolated by the number of nucleoli contained therein and by the diameters of said nucleoli, determining the difference between said cells, and, for the stomach, cervix uteri and lung localizations, said difference is determined between the number of cells containing one or two nucleoli whereof at least one is greater than 2 mcm in diameter, whereas another said difference is determined between the number of cells containing one or two nucleoli less than 2 mcm in diameter and the number of cells containing greater than two nucleoli whereof at least one is greater than 2 mcm in diameter, and, should both said differences be negative in value, the preparation under study is diagnosed as cancerous, whereas should both said differences be positive in value, the preparation under study is diagnosed as precancerous.

6. A method of cytological diagnosis of precancer and cancer, which comprises obtaining cytological preparations containing cells suspected of being atypical; isolating from among the suspect cells of said preparations those cells which contain nucleoli, and isolating therefrom those cells whereof the nucleoli are greater than 2 mcm in diameter; classifying the cells thus isolated by the number of nucleoli contained therein as well as by the diameters of the nucleoli, and determining the difference between said cells, and, for the stomach, cervix uteri and lung localizations, said difference is determined between the number of cells containing one or two nucleoli whereof at least one is greater than 2 mcm in diameter, whereas another said difference is determined between the number of cells containing one or two nucleoli equal in diameter to 2 mcm and the number of cells containing greater than two nucleoli whereof at least one is greater than 2 mcm in diameter, and, should both said differences be negative in value, the preparation under study is diagnosed as cancerous, while should both said differences be positive in value, the preparation under study is diagnosed as precancerous.

7. A method of cytological diagnosis of precancer and cancer, which comprises obtaining cytological preparations containing cells suspected of being atypical; isolating from among the suspect cells of said preparations those cells which contain nucleoli, and isolating therefrom those cells whereof the nucleoli are greater than 2 mcm in diameter; classifying the cells thus isolated by the number of nucleoli contained therein and by the diameters of the nucleoli, and determining for the stomach, cervix uteri and lung localizations, the ratio of the number of cells containing one or two nucleoli equal in diameter to 2 mcm to the number of cells containing one or two nucleoli of which at least one is greater than 2 mcm in diameter, as well as the ratio of the number of cells containing one or two nucleoli smaller than 2 mcm in diameter to the number of cells containing greater than two nucleoli of which at least one is greater than 2 mcm in diameter, and, should both said ratios be smaller than unity, the preparation under study is diagnosed as cancerous, whereas should both said ratios be greater than unity, the preparation under study is diagnosed as precancerous.

8. A method of cytological diagnosis of precancer and cancer, which comprises obtaining cytological preparations containing cells suspected of being atypical; isolating from among the suspect cells of said preparations those cells which contain nucleoli, and isolating therefrom those cells whereof the nucleoli are greater than 2 mcm in diameter; classifying the cells thus isolated by the number of nucleoli contained therein as well as by the diameter of the nucleoli; determining, for the stomach, cervix uteri and lung localizations, the ratio of the number of cells containing one or two nucleoli smaller than 2 mcm in diameter to the number of cells containing one or two nucleoli of which at least one is greater than 2 mcm in diameter, as well as the ratio of the number of cells containing one or two nucleoli smaller than 2 mcm in diameter to the number of cells containing greater than two nucleoli of which at least one is greater than 2 mcm in diameter, and, should both said ratios be smaller than unity, the preparation under study is diagnosed as cancerous, whereas should both said ratios be greater than unity, the preparation under study is diagnosed as precancerous.

9. A method of cytological diagnosis of precancer and cancer, which comprises obtaining cytological preparations containing cells suspected of being atypical; isolating from among the suspect cells of said preparations those cells which contain nucleoli, and isolating therefrom those cells whereof the nucleoli are greater than 2 mcm in diameter; classifying the cells thus isolated by the number of nucleoli contained therein as well as by the diameters of the nucleoli; determining for the stomach, cervix uteri and lung localizations, the ratio of the number of cells containing one or two nucleoli equal to 2 mcm in diameter to the number of cells containing one or two nucleoli of which at least one is greater than 2 mcm in diameter, and the ratio of the number of cells containing one or two nucleoli equal to 2 mcm in diameter to the number of cells containing greater than two nucleoli of which at least one is greater than 2 mcm in diameter, and, should both said ratios be smaller than unity, the preparation under study is diagnosed as cancerous, whereas should both said ratios be greater than unity, the preparation under study is diagnosed as precancerous.

10. A method of cytological diagnosis of precancer and cancer, which comprises obtaining cytological preparations containing cells suspected of being atypical; isolating from among the suspect cells of said preparations those cells which contain nucleoli, and isolating therefrom those cells whereof the nucleoli are greater than 2 mcm in diameter; classifying the cells thus isolated by the number of nucleoli contained therein as well as by the diameters of the nucleoli; then determining, for the stomach, cervix uteri and lung localizations, the ratio of the number of cells containing one or two nucleoli smaller than 2 mcm in diameter to the number of cells containing one or two nucleoli of which at least one is equal to 2 mcm in diameter, and the ratio of the number of cells containing one or two nucleoli equal to 2 mcm in diameter to the number of cells containing greater than two nucleoli of which at least one is greater than 2 mcm in diameter, and, should both said ratios be smaller than unity, the preparation under study is diagnosed as cancerous, whereas should both said ratios be greater than unity, the preparation under study is diagnosed as precancerous.

\* \* \* \* \*